United States Patent
Gray-Dreizler et al.

(10) Patent No.: US 11,480,256 B2
(45) Date of Patent: Oct. 25, 2022

(54) CONDENSATE DRAIN VALVE

(71) Applicant: Aesculap AG, Tuttlingen (DE)

(72) Inventors: John Gray-Dreizler, Niedereschach (DE); Matthias Henke, Fridingen (DE); Andreas Elisch, Dunningen (DE); Stefan Thomas, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 17/285,139

(22) PCT Filed: Nov. 13, 2019

(86) PCT No.: PCT/EP2019/081107
§ 371 (c)(1),
(2) Date: Apr. 14, 2021

(87) PCT Pub. No.: WO2020/099455
PCT Pub. Date: May 22, 2020

(65) Prior Publication Data
US 2021/0356051 A1 Nov. 18, 2021

(30) Foreign Application Priority Data
Nov. 16, 2018 (DE) .................... 10 2018 128 871.9

(51) Int. Cl.
*F16K 24/00* (2006.01)
*A61L 2/26* (2006.01)
(Continued)

(52) U.S. Cl.
CPC ................ *F16K 24/00* (2013.01); *A61L 2/26* (2013.01); *F16K 27/02* (2013.01); *F16K 31/002* (2013.01); *F16K 31/126* (2013.01)

(58) Field of Classification Search
CPC ........ F16K 24/00; F16K 27/02; F16K 31/002; F16K 31/126; A61L 2/26
See application file for complete search history.

(56) References Cited

U.S. PATENT DOCUMENTS

| 5,352,416 A | 10/1994 | Wagner |
| 8,544,381 B2 | 10/2013 | Cartigny et al. |
| (Continued) |

FOREIGN PATENT DOCUMENTS

| CN | 1638678 A | 7/2005 |
| CN | 201135624 | 10/2008 |
| (Continued) |

OTHER PUBLICATIONS

Written Opinion received in International Application No. PCT/EP2019/081107 dated Feb. 7, 2020, with translation, 10 pages.
(Continued)

*Primary Examiner* — Daphne M Barry
(74) *Attorney, Agent, or Firm* — Christopher A. Rothe; Culhane Meadows, PLLC (57) ABSTRACT

A drain valve for a sterile container includes: a valve housing; a bypass that connects a container gas volume with an external gas volume; a valve body that blocks the bypass; and an actuator that displaces the valve body between a passage position and a blocking position. The valve body is displaceable according to a temperature and/or a pressure of the bypass gas volume. The valve housing has: at least one holding web, at least part of which can be located in a holding bracket of the valve receptacle; and a closure. The valve housing is pivotable from an open position into an installation position in which the closure can be fixed to a closure receptacle. When the valve housing is transferred into the installation position, the valve body is transferred into the blocking position and subjected to a closure force.

11 Claims, 4 Drawing Sheets

(51) Int. Cl.
*F16K 27/02* (2006.01)
*F16K 31/00* (2006.01)
*F16K 31/126* (2006.01)

(56) References Cited

U.S. PATENT DOCUMENTS

2018/0177560 A1   6/2018  Weisshaupt
2020/0147252 A1*  5/2020  Mithani .................. A61L 2/206

FOREIGN PATENT DOCUMENTS

| DE | 7640905 U1 | 9/1977 |
| DE | 8532892 U1 | 1/1986 |
| DE | 3838099 C1 | 9/1989 |
| DE | 4111077 A1 | 10/1992 |
| DE | 4111077 C2 | 10/1992 |
| DE | 202010003204 U1 | 7/2010 |
| DE | 102015110419 A1 | 12/2016 |
| EP | 2366410 B1 | 8/2014 |

OTHER PUBLICATIONS

International Search Report received in Application No. PCT/EP2019/081107 dated Feb. 7, 2020 with translation, 3 pages.
Search Report received in German Application No. 10 2018 128 871.9 dated Jul. 19, 2019 with translation, 14 pages.
Wagner GmbH, "Steriset Sterilcontainer" Brochure, copyright date 2017, 12 pages (includes English translations).
Office Action received in Chinese Application No. 201980058345.3 dated Aug. 11, 2021, with translation, 15 pages.

\* cited by examiner

CONDENSATE DRAIN VALVE

CROSS-REFERENCE TO RELATED APPLICATIONS

This application is the United States national phase entry of International Application No. PCT/EP2019/081107, filed Nov. 13, 2019, and claims the benefit of priority of German Application No. 10 2018 128 871.9, filed Nov. 16, 2018. The contents of International Application No. PCT/EP2019/081107 and German Application No. 10 2018 128 871.9 are incorporated by reference herein in their entireties.

FIELD

The present invention relates to a condensate drain valve for a sterile container that can be closed in a gas-tight manner.

BACKGROUND

Sterile containers of the present type are used, among other things, for sterilizing medical instruments. For this purpose, the sterile container has a receiving tray or container tray into which instruments to be sterilized, the sterile goods, can be placed, a container lid for fluid-tight closure of the sterile container, and a closure/closure mechanism (locking mechanism) by means of which the lid can be firmly (fluid-tightly) locked to the container tray.

Furthermore, the sterile container usually has a valve mechanism that prevents the internal container pressure from rising above a predetermined/predeterminable value that may damage the sterile container during a sterilization process in an autoclave. Furthermore, it is known that the valve mechanism can be designed/equipped in such a way that condensate, which accumulates in the sterile container during the sterilization process, can be discharged through the valve mechanism.

From the prior art, for example according to relevant products of the present applicant, (medical) sterile containers of the type as described above are known which have a container tray closable by means of a container lid as well as a closing/locking mechanism via which the lid can be locked in a fluid-tight manner to the tray. A valve device is also provided in the container lid, allowing ambient gas to flow into the container interior via a (sterilizing) filter device and allowing container interior gas to flow out into the environment, bypassing the filter device. In known sterile containers, it is provided that the condensate is transferred into the gas form at the end of the sterilization process in a defined drying phase and is discharged, for example, through a filter material of the sterile container.

Other valve devices known from the prior art are described, for example, in DE 41 11 077 C2 and EP 2 366 410 B1. The valve devices each have an actuator/controlling element by means of which, when a target temperature and/or a target pressure is reached in a gas volume surrounding the actuator/controlling element, a valve body is displaced and thus a condensate outlet is released. Valve devices that have a so-called absolute pressure valve have proven to be particularly advantageous in this respect.

It has proven to be important in the design of valve devices that any interference with the usable space of the sterile container is kept to a minimum,
the valve can be opened only during the sterilization process, and maintenance, assembly and function check of the valve device are as simple as possible.

Furthermore, it would be desirable that the valve device can be checked from the outside without having to open the sterile container,
condensate discharged by the valve device does not run onto other sterile containers that may be located below the sterile container, and
the condensate can already be discharged from the sterile container during the sterilization process.

SUMMARY

In view of the aforementioned description of the prior art, it is the object of the present invention to provide a functional valve device (condensate drain valve) for a/of a sterile container, preferably of the medical type, by means of which the preceding, desirable properties are achievable, if possible all of them.

Accordingly, the present invention relates to a condensate drain valve for arrangement (mounting) in a valve receptacle of a sterile container which can be closed in a gas-tight manner, having a valve housing which has at least one inlet portion which can be/is opened towards a container gas volume surrounded by the sterile container; and at least one outlet portion, which can be/is opened towards an external gas volume surrounding the sterile container at least in sections; a bypass through which the inlet portion and the outlet portion can be/are connected to each other at least in a gas-conducting and/or fluid-conducting manner by means of a bypass gas volume enclosed in sections by the bypass, wherein the bypass gas volume is always in operative connection with at least the container gas volume or the external gas volume; a valve body displaceable between a blocking position and a passing position, via which, in its blocking position, a condensate outlet of the sterile container arranged in the valve receptacle can be/is closed; and at least one actuator which is assigned to the valve body and is surrounded at least in sections by the bypass gas volume and via which the valve body can be/is displaced between the blocking position and the passing position as a function of a temperature and/or a pressure of the bypass gas volume. According to the invention, the valve housing comprises at least one retaining web (forming a type of hinge) and at least one (catch spring-like) closure means spaced from the retaining web, wherein the retaining web can be/is arranged at least in sections in a retaining tab/eyelet of the valve receptacle; and the valve housing can be/is fixed to the valve receptacle so as to be pivotable about a (theoretical) pivot axis aligned parallel to the retaining web, and the valve housing can be pivoted about the pivot axis from an opening position into an installation position in which the closure means can be/is fixed to a closure receptacle of the sterile container; when the valve housing is moved into the installation position, the valve body is moved into the blocking position by the actuator fixed to an actuator receptacle of the valve housing and is subjected to a closing force. The valve body is preferably moved into the opening position by the actuator as soon as the bypass volume reaches an opening pressure and/or an opening temperature. Such a design of the condensate drain valve according to the invention ensures that, in particular during a sterilization process, an exchange of medium between the container gas volume and the external gas volume is possible and condensate can thus be discharged from the sterile container.

Accordingly, the displacement of the valve body by the actuator is independent of pressure and/or temperature conditions generated between the container gas volume and the external gas volume, but only depends on the pressure and/or temperature to which the actuator is subjected by the bypass gas volume surrounding it at least in sections. As soon as the bypass gas volume reaches a target temperature and/or a target pressure, the actuator applies an actuating force, displaces the valve body away from the condensate outlet and thus opens the bypass. According to the basic laws of fluid mechanics, a preferred direction of medium exchange depends on the conditions prevailing in the volumes. If there is an overpressure in the container gas volume, the medium exchange takes place from the container gas volume in the direction of the external gas volume. If there is a negative pressure in the container gas volume, the medium exchange takes place from the external gas volume in the direction of the container gas volume. If the condensate drain valve is open when there is equal pressure between the gas volumes, the medium exchange is subject to the laws of diffusion.

The fact that the valve housing can be pivoted from the installation position (assembly position) to the opening position (disassembly position) in accordance with the idea of the invention means that the condensate drain valve according to the invention can be cleaned, checked and/or serviced in a simple manner.

In order to increase a sealing effect between the valve body and the condensate outlet, it is preferably provided that the valve body can have sealing elements, in particular O-rings, flat seals or the like. Furthermore, it is also possible and provided that the condensate outlet can have a valve seat that is adapted to the valve body in such a way that a continuous sealing surface is formed between the valve body and the valve seat when the valve body is moved into the blocking position, in which the valve body and the valve seat are brought into sealing contact. In order to improve the sealing effect between the valve body and the valve seat, the valve seat can have sealing elements.

In order to enable particularly simple mounting of the actuator, it is provided that the actuator can be fixed to the valve housing by means of a snap-fit connection. In order to at least minimize and preferably prevent unintentional flow around the actuator, it is also advantageously provided that the actuator is additionally fixed to the actuator housing by means of an adhesive fixing process, in particular using a sealing adhesive.

However, it is also possible for the actuator to be detachably fixed to the actuator receptacle. Suitable detachable connections are, for example, screw connections, plug-in connections, latching connections, bayonet-type connections or similar connections. In a condensate drain valve designed in this way, it is in particular advantageous that individual parts of the condensate drain valve, in particular the valve body and the actuator, can be replaced and/or renewed.

In order to improve sealing between the actuator and the actuator receptacle, it is also possible that a sealing element, for example an O-ring, a sealing lip or the like, can be arranged and/or formed between the actuator and the actuator receptacle.

In an advantageous implementation of the idea of the invention, it is provided that the actuator has a bellows/is formed as a bellows by which an actuator gas volume is enclosed and hermetically sealed with respect to the bypass gas volume, so that the bellows is axially expanded or compressed depending on a pressure difference generated between the bypass gas volume and the actuator gas volume. Bellows in the sense of the invention means a substantially cylindrical construction element which is preferably rotationally symmetrical about a longitudinal axis, wherein at least one fold delimiting a first region of the lateral surface from a second region of the lateral surface is arranged on a lateral surface of the bellows, wherein this fold can be used to change an angle formed between the lateral surfaces, or, respectively the lateral surfaces can be tilted relative to each other around the fold, so that a distance between a first cover surface of the bellows and a second cover surface of the bellows can be changed, i.e. the bellows can be stretched and/or compressed. Preferably, the bellows has a plurality of folds.

Since the bellows of the actuator provided according to the invention encloses a preferably hermetically sealed actuator gas volume, it is provided that for stretching and/or compressing the bellows, a pressure of the bypass gas volume surrounding the actuator at least in sections has to be changed in such a way that the actuator gas volume has at least a negative pressure in relation to the bypass gas volume. Furthermore, it is provided that the actuator gas volume, as long as it has an overpressure in relation to the bypass gas volume, contributes by means of the bellows at least proportionally to the closing force exerted by the actuator on the valve body.

In an advantageous embodiment of the condensate drain valve, it is provided that the actuator has a spring element/spring portion via which the expansion and/or compression of the bellows is supported. Such a design of the actuator enables that mechanical properties of the actuator can be adapted. Via the spring element/the spring portion, for example, the closing force can be adjusted independently of further parameters, in particular pressure and/or temperature of the bypass gas volume. It is also possible and provided that the spring element/spring portion can have a variable spring constant so that a spring preload acting on the actuator/bellows can be varied. It is provided that the spring preload can be adjusted in such a way that compression as well as stretching of the bellows can be supported.

It is provided that the spring element can be arranged, for example, within the bellows and in particular acts on the cover surfaces of the bellows. In a particularly advantageous configuration example, it is provided that the spring portion is formed by the lateral surfaces and/or folds of the bellows, for example by locally increasing a material thickness and thus a stiffness.

An advantageous embodiment of the invention provides that the actuator has a bimetallic element acting mechanically on the actuator, via which in particular the closing force can be varied as a function of a temperature of the bypass gas volume. Such a design of the actuator ensures that the closing force is not only dependent on the pressure prevailing in the bypass gas volume. This makes it possible for the closing force exerted by the actuator on the valve body before, during and after the sterilization process to also be set as a function of a temperature, in particular the temperature prevailing in the bypass gas volume. This is advantageous in particular if pressure conditions formed in and around the sterilization container are only insufficiently suitable as the sole parameter for controlling a sealing behavior of the condensate drain valve during the sterilization process.

In order to support in particular uncomplicated installation and removal of the condensate drain valve, it is provided in accordance with the invention that the closure means has at least one spring-loaded latching hook which, when the valve housing is transferred into the installation position, engages at least partially behind a section of the closure receptacle designed as a latching lug. Preferably, the latching hook has a guide surface of ramp-like design which slides along the latching lug when the valve housing is transferred from the opened position to the installation position, wherein the latching hook is displaced against a spring pressure acting on it until the installation position is reached and the latching hook is displaced by the spring pressure in such a way that the latching lug is engaged behind by the latching hook and the valve housing is fixed to the valve receptacle via the latching hook and the latching lug at least in the region of the latching hook and latching lug. Furthermore, a large number of other latching connections are known, all of which are suitable for use as a combination of closure means and closure receptacle of the condensate drain valve according to the invention.

In order to achieve simple operability and releasability of the connection formable/formed by the latching hook and latching lug, it is preferably provided that the latching hook is brought into operative connection with an operating element via which the latching hook can be displaced away from the latching lug so that a form-fit and/or force-fit connection formed between the latching hook and the latching lug can be released by means of the operating element. Particularly preferably, the operating element is designed as a sliding switch that is brought into operative connection with the latching hook directly or via a mechanism. It is also possible for the operating element to be designed as a push switch which is brought into operative connection with a deflection mechanism, wherein an actuating force exerted on the switch is deflected by the deflection mechanism in such a way that the displacement of the latching hook described at the beginning is made possible.

As a further alternative, it can be provided that the closure means has a first fixing element and the closure receptacle has a second fixing element, and the fixing elements are adapted to each other in such a way that a screw connection can be established by means of the fixing elements when the valve housing is transferred to the installation position. Preferably, the closure means designed in this way has a screw recess for passing through a shaft of a screw and the closure receptacle has a threaded recess adapted to the screw with an internal thread, wherein the screw recess and the threaded recess are brought into alignment when the valve housing is moved into the installation position and the screw can be screwed into the internal thread of the threaded recess, so that the valve housing is/can be fixed to the valve receptacle by a screw head of the screw brought into contact with the closure means in an edge region of the screw recess. Furthermore, it is also possible for the screw to be arranged on the closure means in a loss-proof manner. The screw head can have a number of different screw head drives, for example hexagon socket, hexalobular internal, hexagon head, cross recess, slot or similar designs.

An advantageous implementation of the idea of the invention provides that the valve housing has an intake tube extending from the inlet portion to a container bottom of the sterile container, through which condensate can be conveyed out of the sterile container through the inlet portion, bypass, outlet portion and condensate outlet when the valve body is transferred to the passing position and the container gas volume is at an overpressure in relation to the external gas volume through the intake tube. Such a design of the condensate valve ensures that the condensate can be conveyed through the intake tube both hydropneumatically and by utilizing the ejector effect. In hydropneumatic conveying, it is provided that an intake opening arranged in the area of the container bottom is completely immersed in the condensate and an overpressure acting on the condensate prevails in the container gas volume. Conveying using the ejector effect is based on the fact that gas flowing out of the container gas volume, in particular steam, 'entrains' condensate accumulated in the area of the intake opening and thus conveys it out of the sterile container, so that even small quantities of condensate can be conveyed which could not be discharged from the sterile container with purely hydraulic conveying.

An advantageous embodiment of the invention provides that the condensate drain valve is arranged, at least in sections, on a container wall standing on the container bottom. Such an arrangement of the condensate drain valve minimizes a restriction of a usable space available in the sterile container for sterile goods. In a particularly advantageous configuration example of the invention, it is provided that the condensate drain valve is at least partially recessed into the container wall so that the condensate drain valve protrudes as little as possible from the container wall and is thus protected from damage by the sterile material, in particular during transport.

In an advantageous embodiment of the condensate drain valve according to the invention, it is provided that the valve body has a control pin that can be seen/felt/perceived through the condensate outlet when the valve housing is transferred into the installation position and the valve body is transferred into the blocking position, so that an intended installation and/or an intended function of the condensate drain valve can be checked without tools and without access from the container gas volume. Such a design of the condensate drain valve enables a user to check whether the condensate drain valve is installed as intended before the sterilization process begins. Furthermore, after the sterilization process, it is possible to check whether the condensate drain valve is properly closed, so that it can be determined whether the sterile goods are sterile.

The invention also relates to a sterile container with a condensate drain valve of the type described at the beginning.

BRIEF DESCRIPTION OF THE DRAWING FIGURES

The invention is explained in more detail below by means of preferred embodiments with reference to the accompanying figures.

DETAILED DESCRIPTION

The figures show a preferred configuration example of a condensate drain valve 1 according to the invention for use with a sterile container 2, wherein the illustrated sterile container 2 is shown without a container lid and sterile goods for the purpose of improving clarity. The condensate drain valve 1 is arranged in and fixed to a valve receptacle 4 of the sterile container 2. The condensate drain valve 1 has a valve housing 6 which has a retaining web 8 and a closure means 10 spaced from the retaining web 8. The retaining web 8 is arranged in sections in a retaining tab 12 of the valve receptacle 4. The valve housing 6 is fixed to the valve receptacle 4 so that it can be pivoted about a (theoretical) pivot axis 14 oriented parallel to the retaining web 8. The valve housing 6 is pivotable about the pivot axis 14 from an opening position to an installation position. The valve housing 6 of the illustrated condensate drain valve 1 is pivoted into the installation position, in which the closure means 10 is fixed to a closure receptacle 16 of the sterile container 2.

The valve housing 6 has an inlet portion 18 and an outlet portion 20. The inlet portion 18 of the valve housing 6 is open to a container gas volume 22, wherein the outlet portion 20 is open to an external gas volume 26 surrounding the sterile container 2 by means of a condensate outlet 24 of the sterile container 2. Furthermore, the valve housing 6 includes a bypass 28 extending through the valve housing 6. A bypass gas volume 30 is enclosed by the bypass 28. By means of the bypass gas volume 30, the inlet portion 18 and the outlet portion 20 can be/are connected to each other in a gas-conducting and fluid-conducting manner. The bypass gas volume 30 is always in operative connection with the container gas volume 22 in the illustrated configuration example of the condensate drain valve 1.

A valve body 32 displaceable between a blocking position and a passing position is arranged in the bypass 28. An actuator 34, which is fixed to an actuator receptacle 36 of the valve housing 6, is assigned to the valve body 32. As a result of the valve housing 6 being moved into the installation position, the valve body 32 is subjected to a closing force 38 by the actuator 34 and is moved into the blocking position and closes the condensate outlet 24.

The actuator 34 is designed as a bellows and is surrounded in sections by the bypass gas volume 30. Since the bypass gas volume 30 is in operative connection with the container gas volume 22, the pressures generated in the volumes 22, 33 are dependent on each other in an at least a directly proportional manner. During a sterilization process, the temperature of the container gas volume 22 increases and thus, as a result of the hermetic seal of the sterile container 2, its pressure also increases. Due to the direct operative connection between the container gas volume 22 and the bypass gas volume 22 surrounding the actuator 34, the pressure in the bypass gas volume 22 also increases. An actuator gas volume 40 is enclosed by the actuator 34 and hermetically sealed from the bypass gas volume 30. As soon as the pressure of the bypass gas volume 30 exceeds an opening pressure, the actuator 34, which is designed as a bellows, is compressed and an actuating force 42 is exerted on the valve body 32 in the opposite direction to the closing force 38 originally acting on the valve body 32, as a result of which the valve body 32 is transferred from the blocking position to the passing position. It is provided that the opening pressure can be adjusted, for example, by reducing or increasing a pressure formed in the hermetically sealed actuator gas volume 40. The higher the pressure in the actuator gas volume 40 is, the higher the pressure in the bypass gas volume 30 has to be in order to be able to compress the bellows.

In order to realize the most compact design possible, the configuration example of the condensate drain valve 1 shown is arranged on a container wall (side wall) 46 standing on a container base 44 of the sterile container 2.

The valve housing 6 of the condensate drain valve 1 shown has an intake tube (beak) 48 extending from the inlet portion 18 up to the container bottom 44 of the sterile container 2. When the valve body is transferred to the passing position and there is an excess pressure of the container gas volume 22 in relation to the external gas volume 26, condensate in particular can be discharged from the sterile container 2 through the intake tube 48, said condensate having accumulated at the container base 44.

Figure 1:
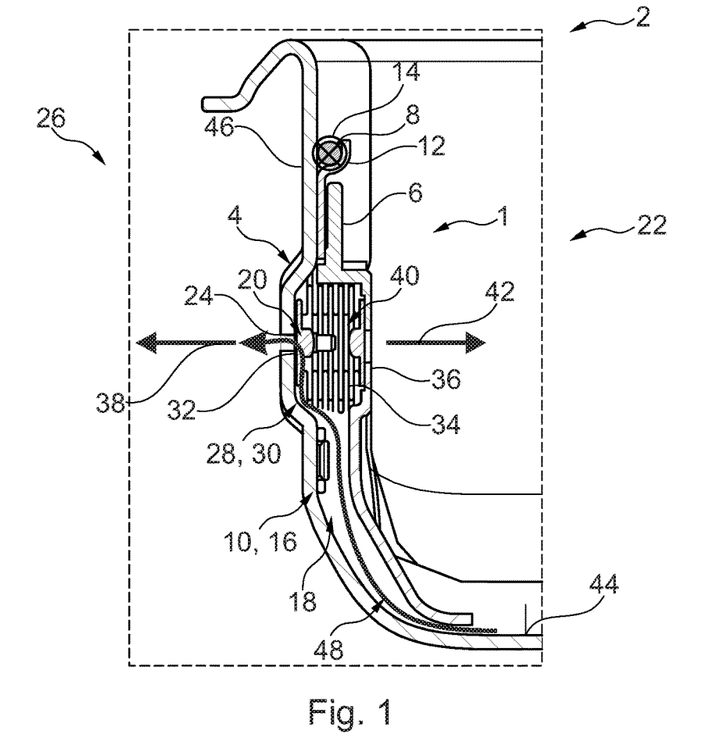
FIG. 1 shows a cross-section of a condensate drain valve inserted in a sterile container.
Figure 2:
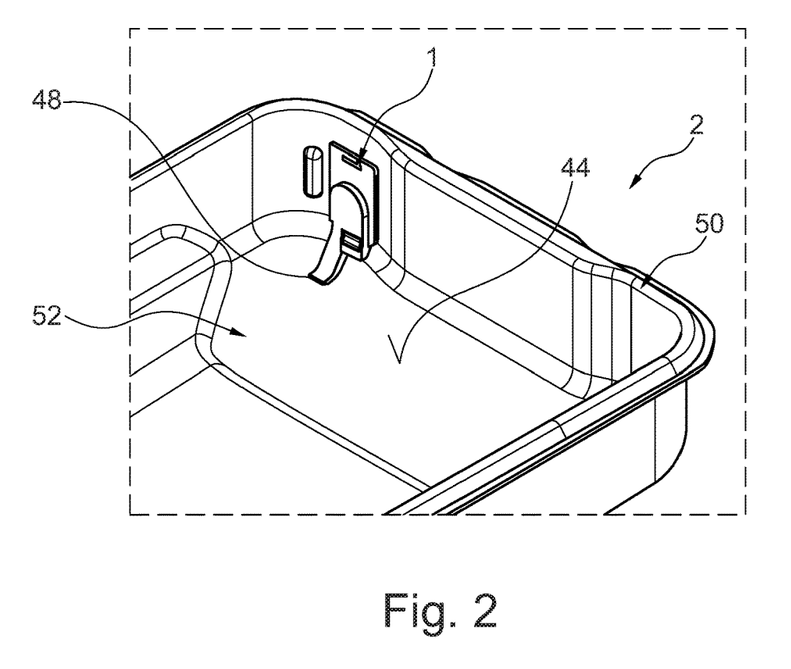
FIG. 2 shows a condensate drain valve inserted in the wall of a sterile container.

FIG. 2 shows the condensate drain valve 1 arranged in a container tray 50 of the sterile container 2 in the installed position. The container tray 50 has a condensate collection channel 52 in the region of the container bottom 44, which extends as far as the intake tube 48 of the condensate drain valve and through which collection of the condensate in the region of the intake tube 48 is facilitated.

Figure 3:
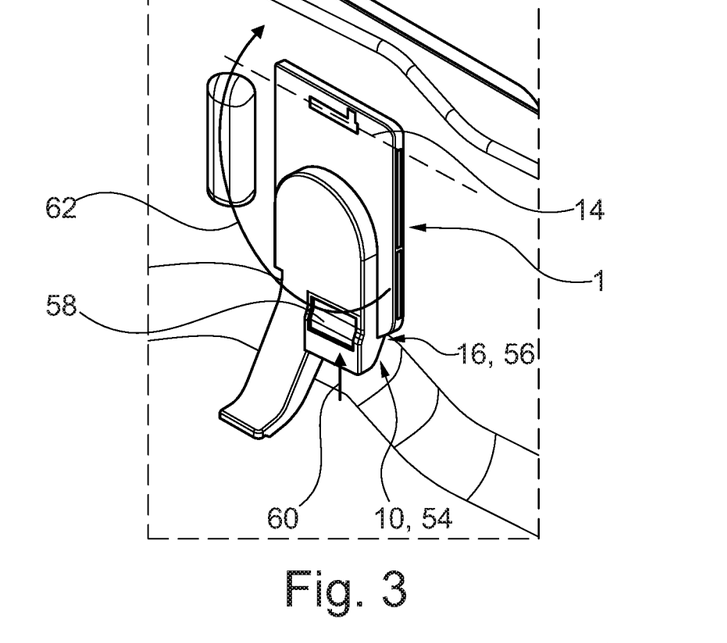
FIG. 3 shows how a condensate drain valve can be transferred from the installation position to the opening position.

FIG. 3 shows an enlarged view of the condensate drain valve 1 already shown in FIG. 2. The figure shows how the condensate drain valve 1 arranged in the installed position can be transferred to the opening position. The closure means 10 has a spring-loaded latching hook 54, via which a section of the closure receptacle 16 formed as a latching nose 56 is in sections engaged from behind. The latching hook 54 is brought into operative connection with an operating element 58 designed as a slide switch. As soon as an actuating force 60 is exerted on the operating element 58, the latching hook 54 is displaced away from the latching nose 56 and the connection between the latching hook 54 and the latching nose 56 is released. The valve housing 6 can then be displaced around the pivot axis 14, along an arc 62 from the installation position to the opening position.

Figure 4:
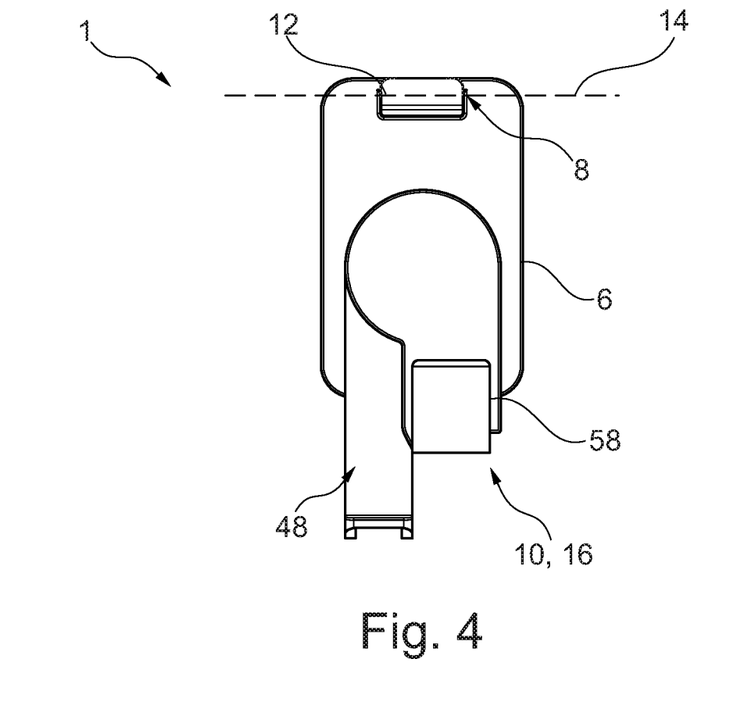
FIGS. 4 and 5 show different views of a removed condensate drain valve.
Figure 5:
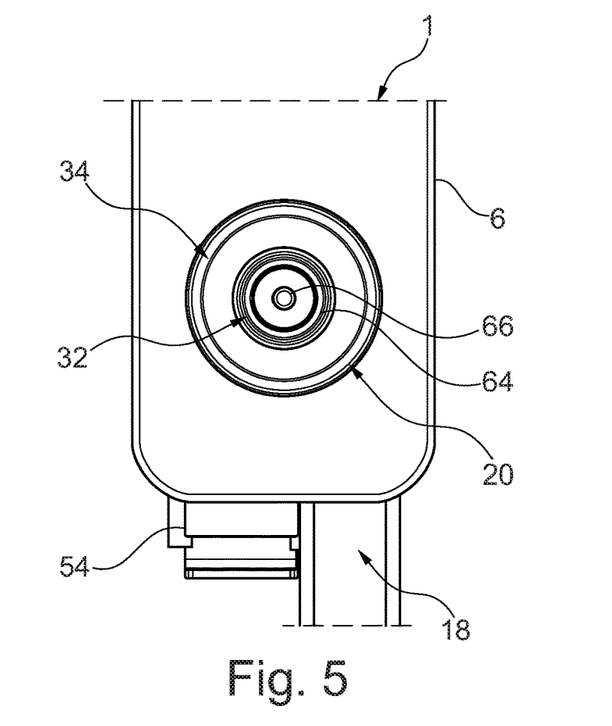

In FIGS. 4 and 5, the condensate drain valve 1 is shown in opposing top views. In FIG. 5, the valve housing 6 is shown with the valve body 32 and a sealing element 64 fixed to the valve body, which is brought into contact with a sealing area arranged circumferentially around the condensate outlet, which is not shown, when the valve body 32 is moved into the blocking position. A control pin 66 is arranged in the center of the valve body 32, which projects through the condensate outlet when the valve body 32 is moved to the blocking position. The figure also shows the inlet portion 18, the outlet portion 20, the actuator 34, and the latching hook 54.

Figure 6:
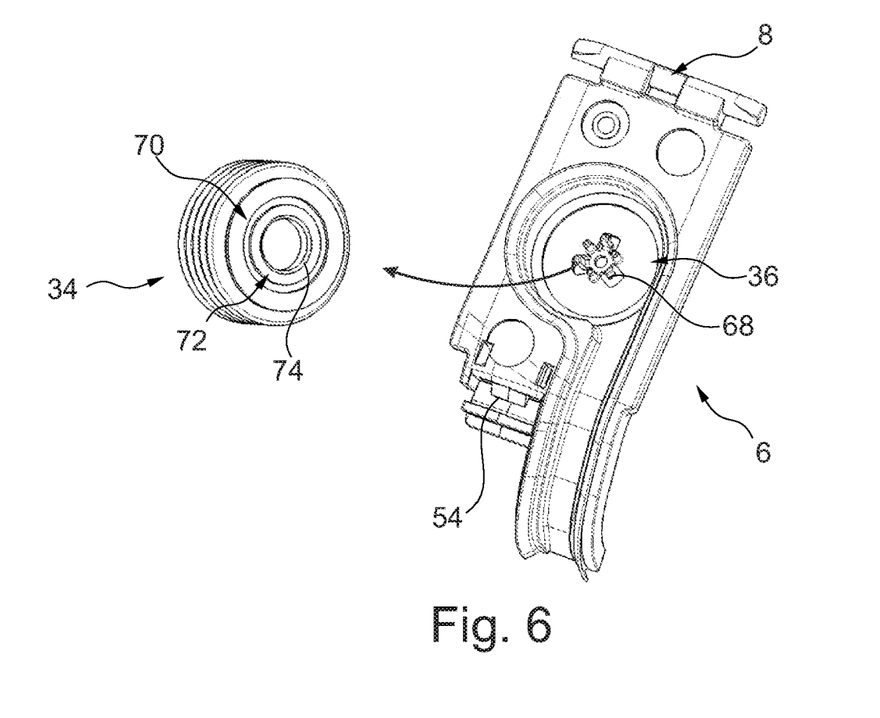
FIG. 6 shows a condensate drain valve with the actuator removed.

In the condensate drain valve 1 shown in FIG. 6 and removed from the sterile container 2, the actuator 34 is separate from the valve housing 6. The valve housing 6 has three snap-fit hooks 68 arranged equidistantly to each other in a circumferential direction in the area of the actuator receptacle 36. The actuator 34 has a circumferential projection 72 in a fixing region 70, which is engaged behind by the snap-fit hooks 68 when the actuator 34 is inserted into the actuator receptacle 36 as intended. In order to fix the actuator 34 to the valve housing 6, the actuator 34 is inserted into the actuator receptacle 36 with the fixing region 70 leading in such a way that the snap-fit hooks 68 are guided past the projection 72 and are brought into contact, at least in sections, with a contact surface 74 facing the external gas volume 26. When the actuator 34 is inserted into the actuator receptacle 36 as intended, a snap-fit connection is formed between the actuator 34 and the valve housing 6 by means of the snap-fit hooks 68, the projection 72 and the contact surface 74 in the fixing region 70. In the figure, the latching hook 54 and the retaining web 8 are shown again for clarity.

Figure 7:
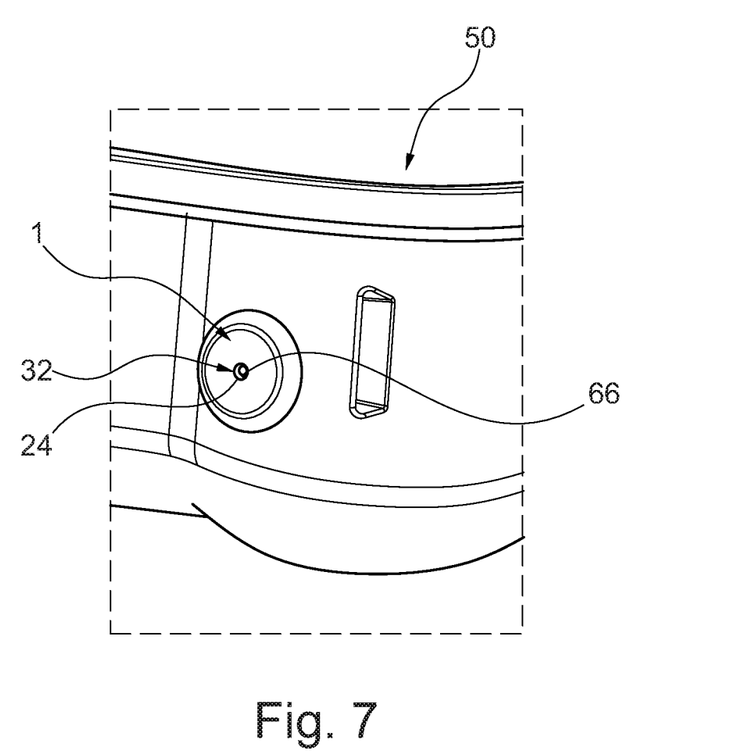
FIG. 7 shows a detailed view of a condensate outlet of a sterile container with a condensate drain valve installed.

FIG. 7 shows an external view of the container tray 50 with a condensate drain valve 1 inserted into the valve receptacle 4. The control pin 66 protrudes through the condensate outlet 24, so that it can be seen that the condensate drain valve 1 has been installed as intended and the valve body 32 has been moved to the blocking position.

The invention claimed is:

1. A condensate drain valve for arrangement in a valve receptacle of a sterile container which can be closed in a gas-tight manner, the condensate drain valve comprising:
a valve housing, which has an inlet portion configured to be open towards a container gas volume enclosed by the sterile container, and an outlet portion configured to be open towards an external gas volume surrounding the sterile container at least in sections;
a bypass, through which the inlet portion and the outlet portion are connected to each other in a gas-conducting and/or fluid-conducting manner by a bypass gas volume enclosed in sections by the bypass, and the bypass gas volume is always in operative connection with at least the container gas volume or the external gas volume;
a valve body displaceable between a blocking position and a passing position and via which, in the blocking position, a condensate outlet of the sterile container arranged in the valve receptacle is configured to be closed; and
at least one actuator which is assigned to the valve body and is surrounded at least in sections by the bypass gas volume and via which the valve body displaceable between the blocking position and the passing position as a function of a temperature and/or a pressure of the bypass gas volume,
wherein,
the valve housing has at least one retaining web and at least one closure spaced apart from the retaining web, wherein the retaining web is arrangeable at least in sections in a retaining tab of the valve receptacle, and the valve housing is fixable to the valve receptacle such that the valve housing is pivotable about a pivot axis aligned parallel to the retaining web,
the valve housing being pivotable around the pivot axis from an opening position to an installation position in which the closure is fixable to a closure receptacle of the sterile container,
when the valve housing is moved into the installation position, the valve body is moved into the blocking position by the actuator fixed to an actuator receptacle of the valve housing and is subjected to a closing force, and
the valve body is transferred to the opening position by the actuator as soon as the bypass gas volume has an opening pressure and/or an opening temperature, so that a medium exchange between the container gas volume and the external gas volume is enabled.

2. The condensate drain valve according to claim 1, wherein the actuator comprises a bellows, by which an actuator gas volume is enclosed and hermetically sealed with respect to the bypass gas volume, so that the bellows is axially expanded or compressed as a function of a pressure difference formed between the bypass gas volume and the actuator gas volume.

3. The condensate drain valve according to claim 2, wherein the actuator comprises a spring element/spring portion by which the expansion and/or compression of the bellows is supported.

4. The condensate drain valve according to claim 1, wherein the actuator has a bimetallic element acting mechanically on the actuator, by which the closing force is variable as a function of a temperature of the bypass gas volume.

5. The condensate drain valve according to claim 1, wherein the closure comprises at least one spring-loaded latching hook by which, when the valve housing is transferred into the installation position, a section of the closure receptacle designed as a latching lug is engaged at least in sections.

6. The condensate drain valve according to claim 5, wherein the latching hook is in operative connection with an operating element via which the latching hook is displaceable away from the latching lug, so that a form-fit and/or force-fit connection formed between the latching hook and the latching lug is releasable by means of the operating element.

7. The condensate drain valve according to claim 1, wherein the closure comprises a first fixing element and the closure receptacle comprises a second fixing element, and the first and second fixing elements are adapted to each other in such a way that, when the valve housing has been moved into the installation position, a screw connection is created by the first and second fixing elements.

8. The condensate drain valve according to claim 1, wherein the valve housing has an intake tube extending from the inlet portion to a container bottom of the sterile container, through which, when the valve body is moved into the passing position and there is an excess pressure of the container gas volume in relation to the external gas volume, condensate is conveyable out of the sterile container through the inlet portion, bypass, outlet portion and condensate outlet through the intake tube.

9. The condensate drain valve according to claim 1, wherein the condensate drain valve is arranged at least in sections on a container wall standing on the container floor.

10. The condensate drain valve according to claim 1, wherein the valve body has a control pin that is detectable through the condensate outlet when the valve housing is moved into the installation position and the valve body is moved into the blocking position, so that an intended installation and/or an intended function of the condensate drain valve is confirmable without tools and without access from the container gas volume.

11. A sterile container with a condensate drain valve according to claim 1.

* * * * *